United States Patent [19]

Dubs et al.

[11] Patent Number: 5,157,141

[45] Date of Patent: Oct. 20, 1992

[54] PROCESS FOR THE PREPARATION OF HYDROXYBENZYLPHOSPHONATES

[75] Inventors: Paul Dubs, Marly; Werner Stegmann, Liestal; Reto Luisoli, Hölstein; Roger Martin, Marly, all of Switzerland

[73] Assignee: Ciba-Geigy Corporation, Ardsley, N.Y.

[21] Appl. No.: 616,549

[22] Filed: Nov. 21, 1990

[30] Foreign Application Priority Data

Nov. 29, 1989 [CH] Switzerland .................. 4271/89

[51] Int. Cl.$^5$ ............................... C07F 9/40
[52] U.S. Cl. ..................... 558/122; 558/104
[58] Field of Search ................ 558/122, 104

[56] References Cited

U.S. PATENT DOCUMENTS

| | | | |
|---|---|---|---|
| 3,006,945 | 10/1961 | Goddard et al. | 558/122 |
| 3,268,630 | 8/1966 | Spivack | 558/122 |
| 3,281,505 | 10/1966 | Spivack | 558/122 |
| 3,787,540 | 1/1974 | Schmidt et al. | 558/122 |
| 3,790,648 | 2/1974 | Schmidt et al. | 558/122 |
| 4,220,760 | 9/1980 | Erckel et al. | 542/460 |

FOREIGN PATENT DOCUMENTS

| | | |
|---|---|---|
| 3030365 | 3/1982 | Fed. Rep. of Germany . |
| 939776 | 10/1963 | United Kingdom ........... 568/122 |

OTHER PUBLICATIONS

Chem. Abstract vol. 97:39143b (1982).

Primary Examiner—James H. Reamer
Attorney, Agent, or Firm—Luther A. R. Hall

[57] ABSTRACT

A process for the preparation of compounds of the general formula I

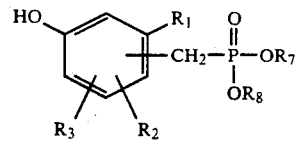

in which $R_1$ is hydrogen or methyl, $R_2$ and $R_3$ independently of one another are $C_1$–$C_{18}$alkyl, $C_5$–$C_8$cycloalkyl, phenyl, $C_7$–$C_9$phenylalkyl or halogen, $R_2$ is additionally hydrogen and $R_7$ and $R_8$ independently of one another are $C_1$–$C_{18}$alkyl, phenyl or $C_7$–$C_{18}$alkylphenyl, which comprises reacting a phenol of the formula II

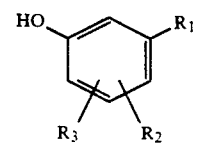

in which $R_1$ to $R_3$ have the meaning described above, with formaldehyde or paraformaldehyde, an amine of the formula III $$NR_4R_5R_6 \qquad \text{III}$$

in which $R_4$ is $C_1$–$C_4$alkyl and $R_5$ and $R_6$ independently of one another are hydrogen or $C_1$–$C_4$alkyl, and a phosphite of the formula IV

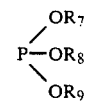

in which $R_7$ and $R_8$ have the meaning described above and $R_9$ has the meaning given for $R_7$ and $R_8$, at a temperature of 0°–200° C.

Some compounds of the formula I are novel.

16 Claims, No Drawings

PROCESS FOR THE PREPARATION OF HYDROXYBENZYLPHOSPHONATES

The present invention relates to a one-step process for the preparation of alkyl-substituted hydroxybenzylphosphonates and some novel hydroxybenzylphosphonates.

The preparation of alkyl-substituted hydroxybenzylphosphonates by multi-step processes is known. Thus, a two-step process is described in GB-A 939,776 and U.S. Pat. Nos. 3,006,945 and 3,281,505 in which, in a first reaction step, an o,o-disubstituted phenol is reacted with formaldehyde and HCl to give the corresponding benzyl chloride which, after its isolation, is reacted in a second reaction step with a trialkyl phosphite to give 3,5-dialkyl-4-hydroxybenzylphosphonate. A process is further known from U.S. Pat. No. 3,268,630 in which, in a first step, the corresponding benzyl alcohol is prepared from the phenol compound and then gives a 3,5-dialkyl-4-hydroxybenzylphosphonate by reaction with triphenyl phosphite and subsequent transesterification with alcohols. Two processes for the preparation of 3,5-dialkyl-4-hydroxybenzylphosphonates are additionally described in U.S. Pat. Nos. 3,790,648 and 3,787,540 in which, in the first, the Mannich base is prepared from the phenol compound with formaldehyde and a secondary amine and then reacted with dialkyl phosphite to give the final compound, while in the second process a dithiourethane is first prepared from the phenol compound using formaldehyde, carbon disulfide and a secondary amine and then, in the second process step, the reaction with dialkyl phosphite to give the final compound is carried out.

These processes are unsatisfactory. On the one hand, the reaction products from the first step must be isolated, which means an outlay in terms of time and material, in that the separated by-products also have to be disposed of. On the other hand, these intermediates, which are also used as starting materials for the second process step, are unstable in some cases or cannot be prepared so easily industrially.

A one-step process for the preparation of hydroxybenzylphosphonates has now surprisingly been found as a result of which the problems of the stability and preparability of the intermediates are lacking and the outlay is simplified.

The present invention relates to a process for the preparation of compounds of the general formula I

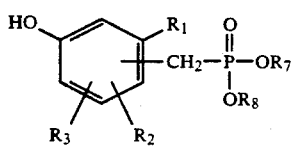

in which $R_1$ is hydrogen or methyl, $R_2$ and $R_3$ independently of one another are $C_1$–$C_{18}$alkyl, $C_5$–$C_8$cycloalkyl, phenyl, $C_7$–$C_9$phenylalkyl or halogen, $R_2$ is additionally hydrogen and $R_7$ and $R_8$ independently of one another are $C_1$–$C_{18}$alkyl, phenyl or $C_7$–$C_{18}$alkylphenyl, which comprises reacting a phenol of the formula II

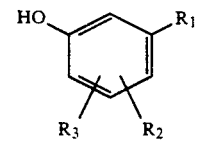

in which $R_1$ to $R_3$ have the meaning described above, with formaldehyde or paraformaldehyde, an amine of the formula III

in which $R_4$ is $C_1$–$C_4$alkyl and $R_5$ and $R_6$ independently of one another are hydrogen or $C_1$–$C_4$alkyl, and a phosphite of the formula IV

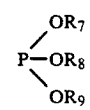

in which $R_7$ and $R_8$ have the meaning described above and $R_9$ has the meaning given for $R_7$ and $R_8$, at a temperature of 0°–200° C.

If $R_4$, $R_5$ and $R_6$ are $C_1$–$C_4$alkyl and $R_2$, $R_3$, $R_7$, $R_8$ and $R_9$ are $C_1$–$C_{18}$alkyl, these are in this case straight-chain or branched alkyl radicals, for example methyl, ethyl, n-propyl, isopropyl, n-butyl, isobutyl, sec-butyl and tert-butyl. $R_2$, $R_3$, $R_7$, $R_8$ and $R_9$ can additionally also be straight-chain or branched pentyl, hexyl, heptyl, octyl, nonyl, decyl, undecyl, dodecyl, tridecyl, tetradecyl, pentadecyl, heptadecyl and octadecyl.

If $R_2$ and $R_3$ are $C_5$–$C_8$cycloalkyl, they are, for example, cyclopentyl, cyclohexyl, cycloheptyl or cyclooctyl, preferably cyclohexyl.

If $R_2$ and $R_3$ are $C_7$–$C_9$phenylalkyl, they are, for example, benzyl, 1- or 2-phenethyl, 3-phenylpropyl, α,α-dimethylbenzyl or 2-phenylisopropyl, but preferably benzyl.

If $R_2$ and $R_3$ are halogen, they are, for example, fluorine, chlorine, bromine or iodine, preferably chlorine.

If $R_7$, $R_8$ and $R_9$ are $C_7$–$C_{18}$alkylphenyl, they are, for example, phenyl substituted by one or more, preferably 1 to 3, in particular 1 or 2, $C_1$–$C_{12}$alkyl groups, but preferably simply alkyl-substituted phenyl; $C_1$–$C_{12}$alkyl is, for example, methyl, ethyl, n-propyl, isopropyl, n-butyl, isobutyl, sec-butyl, tert-butyl, straight-chain or branched nonyl or dodecyl.

The compounds of the general formula I in which $R_1$ is hydrogen or methyl, preferably hydrogen, $R_2$ is cyclohexyl, methyl or tert-butyl and $R_3$ is cyclohexyl (=compounds of the formula Ia), are novel. The present invention therefore also relates to these compounds of the general formula Ia. An example of compounds of the formula Ia is diethyl 3,5-di-cyclohexyl-4-hydroxybenzylphosphonate.

Phenols of the formula II in which $R_1$ is hydrogen are preferably employed in the process according to the invention.

Phenols of the formula II are also preferably employed in which $R_2$ and $R_3$ independently of one another are $C_1$–$C_{18}$alkyl, cyclohexyl, phenyl or benzyl, but particularly preferably $C_1$–$C_4$alkyl or cyclohexyl and especially preferably methyl, tert-butyl or cyclohexyl and $R_2$ is additionally hydrogen.

Of interest are phenols of the formula II in which the radicals $R_2$ and $R_3$ are in the ortho-position to the phenolic hydroxyl group. Preferably, $R_2$ and $R_3$ are different from hydrogen.

Of especial interest are phenols of the formula II in which $R_2$ and $R_3$ are tert-butyl.

In the compounds of the formula I, the

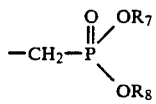

group is preferably in the p-position to the OH group.

Formaldehyde employed in a suitable form in the process according to the invention is, for example, formaldehyde in aqueous solution or paraformaldehyde, preferably paraformaldehyde.

Amines of the formula III employed in the process according to the invention are preferably those in which $R_4$ is methyl, ethyl, propyl or butyl, $R_5$ is hydrogen, methyl, ethyl, propyl or butyl and $R_6$ is hydrogen.

Especially preferred amines of the formula III which are employed are dimethylamine, diethylamine, dipropylamine and dibutylamine.

Phosphites of the formula IV in which $R_7$, $R_8$ and $R_9$ independently of one another are $C_1$-$C_4$alkyl, phenyl or $C_7$-$C_9$alkylphenyl, in particular methyl, ethyl or phenyl, are preferably employed in the process according to the invention.

Phosphites of the formula IV in which $R_7$, $R_8$ and $R_9$ independently of one another are $C_{18}$alkyl or $C_{15}$alkylphenyl are also preferably employed in the process according to the invention.

A phenol of the formula II in which $R_1$ is hydrogen in the 3-position and $R_2$ and $R_3$ are tert-butyl in the 2- and 6-position is very particularly preferably reacted in the process according to the invention with paraformaldehyde, an amine of the formula III in which $R_4$ and $R_5$ are methyl and $R_6$ is hydrogen, and a phosphite of the formula IV in which $R_7$, $R_8$ and $R_9$ are ethyl, in the presence of a solvent or without solvent, in particular without solvent.

If the process according to the invention is carried out in a solvent, suitable solvents are in particular non-polar aprotic solvents, for example aromatic or aliphatic hydrocarbons, for example toluene and ligroin, polar protic solvents, for example monohydric or polyhydric alcohols or ethers, for example methanol and methylcellosolve, polar aprotic solvents, for example dimethylformamide or DMSO or mixtures of non-polar aprotic and polar aprotic solvents. Polar aprotic solvents, in particular dimethylformamide, are preferably employed as solvents.

The process according to the invention is especially preferably carried out without solvent.

The reaction temperature at which the compounds of the formulae II, III and IV and formaldehyde are reacted with one another in suitable form depends in particular on these compounds and on whether the reaction is carried out with or without solvent. The process according to the invention is carried out at a temperature of 0°-200° C., preferably at 80°-150° C. and in particular at 80°-120° C.

Depending on the specific phenol or phosphite, the reaction times vary, for example, between 1 and 12 hours.

The starting substances of the formulae II and IV and the formaldehyde components are expediently reacted in approximately equimolar amounts. However, the compound of the formula IV and the formaldehyde components can also be employed in an excess up to a ratio of phenol:formaldehyde:phosphite of 1:3:4. A ratio of 1:1:1 to 1:2:2 is preferred.

The amount of amine of the formula III employed is in general 1-250 mol-% relative to the phenol of the formula II, preferably 25-125 mol-%, in particular 40-125 mol-%.

The reaction product is worked up in a manner known per se. Depending on the system employed, the following working-up methods, for example, can be used:

removal of the volatile components including the water formed in the reaction by distillation at reduced pressure.

extraction with a water-immiscible organic solvent such as, for example, hexane, heptane, toluene, ethyl acetate or methylene chloride, washing one or more times with water and subsequent evaporation of the dried, separated organic phase.

Depending on the product, other possible subsequent purification processes, for example recrystallization or chromatographic processes, can be used.

The compounds prepared by the process according to the invention are outstandingly suitable as stabilizers against thermo-oxidative and/or photo-induced degradation for a multiplicity of organic monomers and polymers, as described, for example, in U.S. Pat. Nos. 3,280,070, 3,281,505 and 3,367,870.

The examples below further illustrate the present invention. Parts and percentages therein and in the remainder of the description relate to weight, if not stated otherwise.

EXAMPLE 1

Preparation of diethyl 3,5-di-tert-butyl-4-hydroxybenzylphosphonate in solution

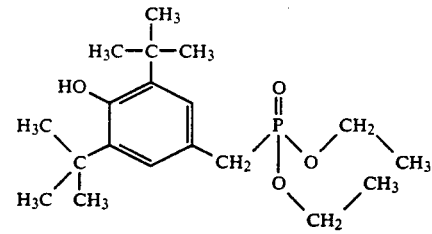

20.63 g (100 mmol) of 2,6-di-tert-butylphenol, 5.22 g (174 mmol) of paraformaldehyde, 6.1 g (45 mmol) of 33% ethanolic dimethylamine and 26 ml (=24.7 g) of N,N-dimethylformamide are heated at 50° C. under nitrogen for 1 hour in a sulfonation flask fitted with a reflux condenser and mechanical stirrer. 33.23 g (200 mmol) of triethyl phosphite are added to this mixture. It is heated under reflux at a reaction temperature of 105° C.; the conversion to the final product is 82% (HPLC). Working-up: extraction (water/methylcyclohexane) and recrystallization (methylcyclohexane). Yield: 23.0 g (65%), melting point 120° C., purity (HPLC): 98%.

| Microanalysis: | C | H | P |
|---|---|---|---|
| calculated: | 64.02 | 9.33 | 8.69% |

| Microanalysis: | C | H | P |
|---|---|---|---|
| found: | 64.26 | 9.53 | 8.7% |

EXAMPLE 2

The procedure is as in Example 1, 6.2 g (48 mmol) of dibutylamine being employed as the amine instead of dimethylamine and 20 ml of a 1:1 mixture of DMF/toluene being employed as the solvent; a conversion of 88% (HPLC) is obtained for the same product as in Example 1. After working-up (extraction with water/toluene and recrystallization from ligroin), 27.2 g (79%) of product are obtained, melting point 120° C., purity (HPLC): 98%.

EXAMPLE 3

Preparation of diethyl 3,5-di-tert-butyl-4-hydroxybenzylphosphonate (solvent-free)

3.2 g of HTMP (hydroxymethylpiperidine), 52.3 g of paraformaldehyde and 206.3 g of 2,6-di-tert-butylphenol are rendered inert and are initially introduced at 60° C. under reduced pressure into a double-jacketed flask with an outlet at the bottom, a baffle, an impeller stirrer and a sublevel air lock for gas introduction. 52 g of dimethylamine gas are introduced at this temperature and the mixture is stirred at 85° C. for 1 hour. Addition of 332 g of triethyl phosphite is then carried out, after which the reaction mixture is kept at 115° C. for 4 hours. Working-up:distillation of triethyl phosphite and dimethylamine under reduced pressure and crystallization of the residue from ligroin yield 320 g of product (90%), melting point 114° C.

EXAMPLE 4

Preparation of diethyl 3,5-di-cyclohexyl-4-hydroxybenzylphosphonate

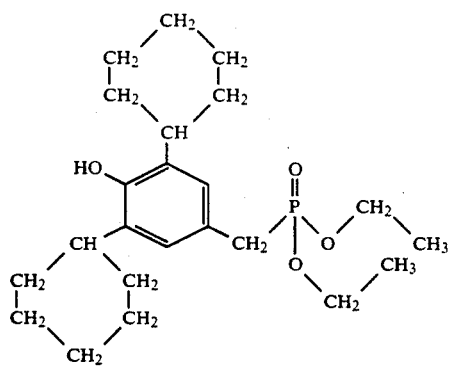

The process is as in Example 1, 25.8 g of 2,6-dicyclohexylphenol being used instead of 2,6-di-tert-butylphenol as the phenol; a conversion of 76% (HPLC) is achieved. After working-up (extraction with water/methylcyclohexane and recrystallization from methylcyclohexane), 16.6 g (42%) of product are obtained, melting point 120° C., purity (HPLC): 96%.

| Microanalysis: | C | H | P |
|---|---|---|---|
| calculated: | 67.62 | 9.13 | 7.58% |

| Microanalysis: | C | H | P |
|---|---|---|---|
| found: | 68.45 | 9.17 | 7.8% |

EXAMPLE 5

Preparation of diphenyl 3,5-di-tert-butyl-4-hydroxybenzylphosphonate

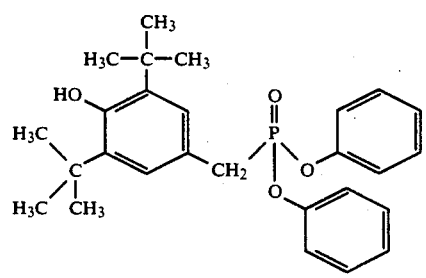

The procedure is as in Example 1, the solvent (ethanol) being dispensed with and 8.1 g of dipropylamine instead of dimethylamine and 55.9 g of triphenyl phosphite instead of triethyl phosphite being used; after working-up (extraction with water/hexane and recrystallization from hexane), 24.3 g (54%) of product are obtained, melting point 130° C., purity (HPLC): 98%.

| Microanalysis: | C | H | P |
|---|---|---|---|
| calculated: | 71.66 | 7.35 | 6.84% |
| found: | 71.75 | 7.46 | 6.9% |

EXAMPLE 6

Preparation of dimethyl 3,5-di-tert-butyl-4-hydroxybenzylphosphonate

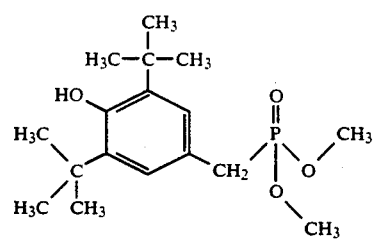

The procedure is as in Example 5, triphenyl phosphite being replaced by 22.3 g of trimethyl phosphite; after working-up (extraction with water/methylcyclohexane and recrystallization from isopropanol), 19.2 g (59%) of product are obtained, melting point 155° C., purity (HPLC): 85%.

| Microanalysis: | C | H | P |
|---|---|---|---|
| calculated: | 62.18 | 8.90 | 9.43% |
| found: | 61.57 | 8.81 | 9.4% |

EXAMPLE 7

Preparation of diethyl 3,5-dimethyl-4-hydroxybenzylphosphonate

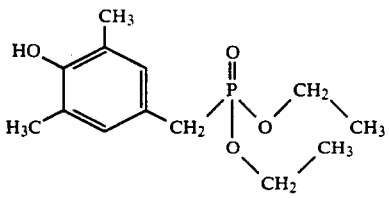

The procedure is as in Example 1, but the 2,6-di-tert-butylphenol being replaced by 12.2 g of 2,6-dimethylphenol; a conversion of 82% (HPLC) is achieved. After working-up (extraction with water/methylcyclohexane and chromatography on silica gel), 13.8 g (51%) of product are obtained, melting point 65° C., purity (HPLC): 98%.

| Microanalysis: | C | H | P |
|---|---|---|---|
| calculated: | 57.35 | 7.77 | 11.38% |
| found: | 57.36 | 7.79 | 11.3% |

EXAMPLE 8

Preparation of diisopropyl 2,6-di-tert-butyl-4-hydroxybenzylphosphonate

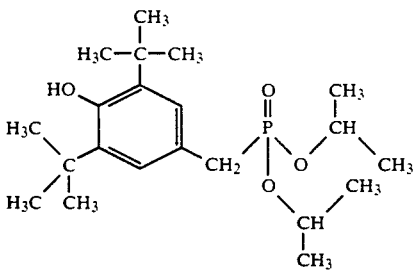

The procedure is as in Example 5, the triphenyl phosphite being replaced by 28.2 g of triisopropyl phosphite; a conversion of 95% (HPLC) is achieved. After working-up (extraction with water/hexane and recrystallization from hexane), 21.1 g (55%) of product are obtained, melting point 100° C., purity (HPLC): 97%.

| Microanalysis: | C | H | P |
|---|---|---|---|
| calculated: | 65.60 | 9.70 | 8.06% |
| found: | 65.67 | 9.74 | 8.0% |

EXAMPLE 9

Preparation of diisopropyl 2,6-dicyclohexyl-4-hydroxybenzylphosphonate

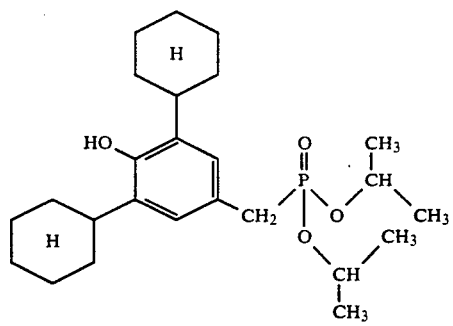

25.84 g (100 mmol) of 2,6-dicyclohexylphenol, 5.22 g (174 mmol) of paraformaldehyde, 8.1 g of dipropylamine and 50 g (240 mmol) of triisopropyl phosphite are processed analogously to Example 1; a conversion of 72% (HPLC) is achieved. After working-up (extraction with water/hexane and recrystallization from hexane), 13.7 g (31%) of product are obtained, melting point 143° C., purity (HPLC): 96%.

| Microanalysis: | C | H | P |
|---|---|---|---|
| calculated: | 68.78 | 9.47 | 7.09% |
| found: | 69.09 | 9.54 | 7.1% |

EXAMPLE 10

Preparation of dibutyl 2,6-dicyclohexyl-4-hydroxybenzylphosphonate

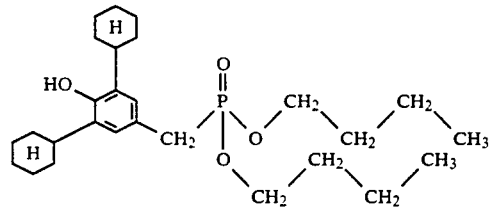

The procedure is as in Example 9, triisopropyl phosphite being replaced by 46.3 g of tributyl phosphite. After working-up (extraction with water, 2N HCl/hexane), 44 g (99%) of liquid product are obtained, purity (HPLC): 74%.

EXAMPLE 11

Preparation of diethyl 2-cyclohexyl-6-methyl-4-hydroxybenzylphosphonate

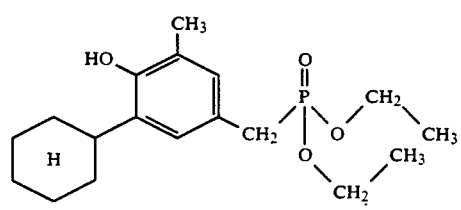

The procedure is as in Example 1, but the 2,6-di-tert-butylphenol being replaced by 19.0 g of 2-cyclohexyl-6-methylphenol; a conversion of 69% (HPLC) is achieved. After working-up (extraction with water/methylcyclohexane and recrystallization from methylcyclohexane), 7.0 g (20%) of product are obtained, melting point 73° C., purity (HPLC): 96%.

| Microanalysis: | C | H | P |
|---|---|---|---|
| calculated: | 63.51 | 8.59 | 9.10% |
| found: | 63.86 | 8.71 | 9.0% |

EXAMPLE 12

Preparation of diisooctyl 2,4-di-tert-butyl-4-hydroxybenzylphosphonate (isomer mixture)

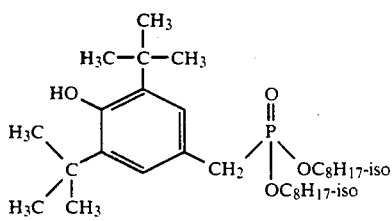

The procedure is as in Example 5, the triphenyl phosphite being replaced by 75.3 g of triisooctyl phosphite (isomer mixture); after working-up (extraction with water/ethyl acetate and chromatography on silica gel), 12.8 g (64%) of product are obtained, purity (HPLC): 96% isomer mixture.

| Microanalysis: | C | H | P |
|---|---|---|---|
| calculated: | 70.95 | 10.95 | 5.90% |
| found: | 70.43 | 11.41 | 5.8% |

EXAMPLE 13

Preparation of diisodecyl 2,4-di-tert-butyl-4-hydroxybenzylphosphonate (isomer mixture)

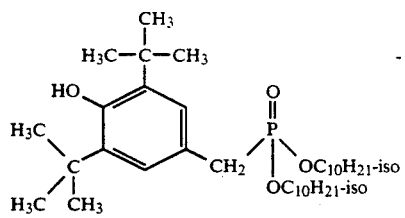

The procedure is analogous to Example 5, the triphenyl phosphite being replaced by 59.3 g of triisodecyl phosphite (isomer mixture); after working-up (extraction with water/ethyl acetate and chromatography on silica gel), 33.8 g (58%) of product are obtained, purity (HPLC): 96% isomer mixture.

| Microanalysis: | C | H |
|---|---|---|
| calculated: | 72.37 | 11.28% |
| found: | 72.10 | 11.7% |

EXAMPLE 14

Preparation of didodecyl 2,6-di-tert-butyl-4-hydroxybenzylphosphonate

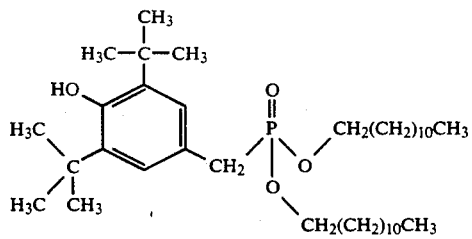

The procedure is as in Example 5, the triphenyl phosphite being replaced by 117.4 g of tridodecyl phosphite; after working-up (extraction with water/ethyl acetate and chromatography on silica gel), 46 g (72%) of product are obtained, purity (HPLC): ~75%.

| Microanalysis: | C | H |
|---|---|---|
| calculated: | 73.54 | 11.55% |
| found: | 74.27 | 12.6% |

EXAMPLE 15

Preparation of dioctadecyl 2,6-di-tert-butyl-4-hydroxybenzylphosphonate

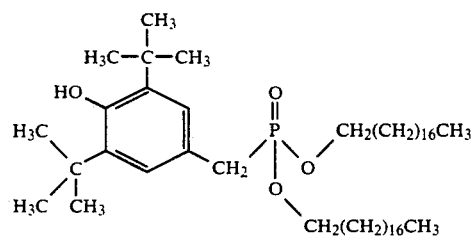

The procedure is as in Example 5, the triphenyl phosphite being replaced by 98.6 g of trioctadecyl phosphite; after working-up (extraction with water/ethyl acetate and chromatography on silica gel), 59 g (73%) of product are obtained, purity (HPLC): ~98%.

| Microanalysis: | C | H |
|---|---|---|
| calculated: | 76.07 | 12.14% |
| found: | 77.87 | 12.92% |

What is claimed is:

1. A process for the preparation of a compound of the general formula I

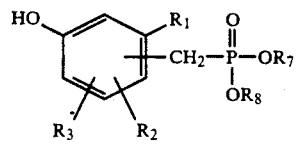

in which $R_1$ is hydrogen or methyl, $R_2$ and $R_3$ independently of one another are $C_1$-$C_{18}$alkyl, $C_5$-$C_8$cycloalkyl, phenyl, $C_7$-$C_9$phenylalkyl or halogen, $R_2$ is additionally hydrogen and $R_7$ and $R_8$ independently of one another are $C_1$–$C_{18}$alkyl, phenyl or $C_7$–$C_{18}$alkylphenyl, which comprises reacting a phenol of the formula II

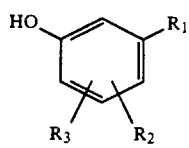 II in which $R_1$ to $R_3$ have the meaning described above, with formaldehyde or paraformaldehyde, an amine of the formula III

 III in which $R_4$ is $C_1$–$C_4$alkyl and $R_5$ and $R_6$ independently of one another are hydrogen or $C_1$–$C_4$alkyl, and a phosphite of the formula IV

 IV in which $R_7$ and $R_8$ have the meaning described above and $R_9$ has the meaning given for $R_7$ and $R_8$, at a temperature of 0°–200° C.

2. A process according to claim 1, wherein $R_1$ is hydrogen.

3. A process according to claim 1, wherein $R_2$ and $R_3$ independently of one another are $C_1$–$C_{18}$alkyl, cyclohexyl, phenyl or benzyl and $R_2$ is additionally hydrogen.

4. A process according to claim 1, wherein $R_2$ and $R_3$ are in the ortho-position to the phenolic hydroxyl group.

5. A process according to claim 3, wherein $R_2$ and $R_3$ are tert-butyl.

6. A process according to claim 1, wherein the reaction is carried out using paraformaldehyde.

7. A process according to claim 1, wherein the amine of the formula III $R_4$ is methyl, ethyl, propyl or butyl, $R_5$ is hydrogen, methyl, ethyl, propyl or butyl, and $R_6$ is hydrogen.

8. A process according to claim 1, wherein $R_7$, $R_8$ and $R_9$ independently of one another are $C_1$–$C_4$alkyl, phenyl or $C_7$–$C_9$alkylphenyl.

9. A process according to claim 1, wherein $R_7$, $R_8$ and $R_9$ independently of one another are $C_{18}$alkyl or $C_{15}$alkylphenyl.

10. A process according to claim 1, wherein a phenol of the formula II in which $R_1$ is hydrogen in the 3-position and $R_2$ and $R_3$ are tert-butyl in the 2-and 6-position is reacted with paraformaldehyde, an amine of the formula III in which $R_4$ and $R_5$ are methyl and $R_6$ is hydrogen, and a phosphite of the formula IV in which $R_7$, $R_8$ and $R_9$ are ethyl.

11. A process according to claim 1, which is carried out in a solvent.

12. A process according to claim 11, wherein the solvent is a polar aprotic solvent.

13. A process according to claim 1, which is carried out without solvent.

14. A process according to claim 1, wherein the reaction temperature is 80°–150° C.

15. A process according to claim 1, wherein the ratio of phenol of the formula II: formaldehyde:phosphite of the formula IV is 1:1:1 to 1:3:4.

16. A process according to claim 1, wherein the amount of amine of the formula III employed is 1–250 mol-% relative to the phenol of the formula II.

* * * * *